(12) United States Patent
Zhang et al.

(10) Patent No.: US 9,805,504 B2
(45) Date of Patent: Oct. 31, 2017

(54) IMAGE DISPLAY METHODS (71) Applicant: Nuctech Company Limited, Beijing (CN)

(72) Inventors: Li Zhang, Beijing (CN); Zhiqiang Chen, Beijing (CN); Qingping Huang, Beijing (CN); Yunda Sun, Beijing (CN); Zhi Tang, Beijing (CN); Le Shen, Beijing (CN); Hu Tang, Beijing (CN); Qianlu Ren, Beijing (CN); Xin Jin, Beijing (CN)

(73) Assignee: Nuctech Company Limited, Beijing (CN)

( * ) Notice: Subject to any disclaimer, the term of this patent is extended or adjusted under 35 U.S.C. 154(b) by 228 days.

(21) Appl. No.: 14/711,949

(22) Filed: May 14, 2015

(65) Prior Publication Data

US 2015/0332498 A1 Nov. 19, 2015

(30) Foreign Application Priority Data

May 14, 2014 (CN) .......................... 2014 1 0202944

(51) Int. Cl.
*H05G 1/64* (2006.01)
*G06T 17/00* (2006.01)
(Continued)

(52) U.S. Cl.
CPC .............. *G06T 17/00* (2013.01); *A61B 6/032* (2013.01); *A61B 6/463* (2013.01); *A61B 6/466* (2013.01);
(Continued)

(58) Field of Classification Search
CPC ......... A61B 6/032; A61B 6/463; A61B 6/466; A61B 6/5205; A61B 6/5223; A61B 6/027;
(Continued)

(56) References Cited

U.S. PATENT DOCUMENTS

| 5,796,802 A | 8/1998 | Gordon |
| 8,180,139 B2 * | 5/2012 | Basu .................... G01V 5/0041 378/57 |

(Continued)

FOREIGN PATENT DOCUMENTS

| CN | 2774421 Y | 4/2006 |
| CN | 1783098 A | 6/2006 |

(Continued)

OTHER PUBLICATIONS

Office Action for Japanese Patent Application No. 2015-099504, dated Jun. 7, 2016, 4 pages.

(Continued)

*Primary Examiner* — Irakli Kiknadze
(74) *Attorney, Agent, or Firm* — Westman, Champlin & Koehler, P.A.

(57) ABSTRACT

The present disclosure discloses an image display method in a CT system. The method comprises: implementing CT scanning on an inspected object, to obtain CT projection data; organizing the CT projection data according to a predetermined interval; extracting basic data from the organized CT projection data by using a fixed angle as a start angle and using 360 degrees as an interval; forming a DR image based on the extracted basic data; reconstructing a three-dimensional image of the inspected object from the CT projection data; and displaying the DR image and the reconstructed three-dimensional image on a screen at the same time. In the solution, the CT data is processed to obtain DR data. After the DR data is obtained, a DR image is obtained directly using a DR data processing algorithm. This enables an image recognizer to more accurately and more rapidly inspect goods carried by a passenger using the existing experience in image recognition of the DR image.

20 Claims, 6 Drawing Sheets (51) Int. Cl.
  *A61B 6/03* (2006.01)
  *A61B 6/00* (2006.01)
  *G06T 19/00* (2011.01)
  *G06T 11/00* (2006.01)
  *G01N 23/04* (2006.01)

(52) U.S. Cl.
  CPC ......... *A61B 6/5205* (2013.01); *G01N 23/046* (2013.01); *G06T 11/003* (2013.01); *G06T 19/003* (2013.01); *A61B 6/5223* (2013.01); *G06T 2207/10081* (2013.01); *G06T 2207/10124* (2013.01); *G06T 2207/30004* (2013.01); *G06T 2207/30196* (2013.01); *G06T 2210/41* (2013.01); *G06T 2211/436* (2013.01); *G06T 2219/016* (2013.01); *G06T 2219/028* (2013.01); *G06T 2219/2004* (2013.01)

(58) Field of Classification Search
  CPC ... G01N 23/046; G06T 11/005; G06T 11/006; G06T 2211/421; G06T 11/003; G06T 17/00; G06T 19/003; G06T 2207/10081; G06T 2207/10124; G06T 2207/30004; G06T 2207/30196; G06T 2210/41; G06T 2211/436; Y10S 378/901
  USPC ........ 382/154, 128, 131, 132; 378/4, 19, 62, 378/98
  See application file for complete search history.

(56) References Cited

U.S. PATENT DOCUMENTS

| | | | |
|---|---|---|---|
| 2003/0219093 | A1 | 11/2003 | Hagiwara |
| 2006/0291717 | A1* | 12/2006 | Mussack ................ A61B 6/032 382/154 |
| 2007/0216681 | A1* | 9/2007 | Nishida ................... G06F 17/50 345/427 |
| 2008/0285853 | A1* | 11/2008 | Bressan ................. G06T 5/009 382/169 |
| 2009/0168959 | A1* | 7/2009 | Chen .................... G01V 5/0041 378/57 |
| 2011/0255763 | A1* | 10/2011 | Bogoni ................. G06T 19/00 382/131 |

FOREIGN PATENT DOCUMENTS

| | | |
|---|---|---|
| CN | 101936924 A | 1/2011 |
| JP | H10-90202 A | 4/1998 |
| JP | 2000-107173 A | 4/2000 |

OTHER PUBLICATIONS

International Search Report and Written Opinion for International Application No. PCT/CN2015/078950, dated Aug. 17, 2015, 9 pages.
English translation of Box No. V of the Written Opinion for the International Search Report of the Written Opinion for International Application No. PCT/CN2015/078950, 2 pages.

* cited by examiner

ARRAY OF DETECTORS 1  2  3  4  ......  N

1st degree
361th degree
721th degree
1081th degree

Fig. 6

S71: CT SCANNING IS IMPLEMENTED ON AN INSPECTED OBJECT, TO OBTAIN CT PROJECTION DATA

S72: A THREE-DIMENSIONAL IMAGE OF THE INSPECTED OBJECT IS RECONSTRUCTED FROM THE CT PROJECTION DATA

S73: DATA OF THE THREE-DIMENSIONAL IMAGE H(X,Y,Z) OF THE INSPECTED OBJECT IS PROJECTED IN A CERTAIN ANGLE OF VIEW, TO OBTAIN DR DATA IN THE ANGLE OF VIEW

S74: A DR IMAGE IS FORMED BASED ON THE DR DATA IN THE ANGLE OF VIEW

S75: THE DR IMAGE AND A THREE-DIMENSIONAL IMAGE ARE DISPLAYED ON A SCREEN AT THE SAME TIME

IMAGE DISPLAY METHODS

TECHNICAL FIELD

The present disclosure relates to the Computed Tomography (CT) imaging technology, and in particular, to an image display method in a CT system.

BACKGROUND

After the American 911 events, more and more attention is paid to security inspection in the aviation field. The CT technology-based security inspection products have incomparable advancements and obviously advantageous performance indices. The American Transportation Standardization Agency (TSA) considers that CT devices and detection methods thereof are important ways to implement security inspection at the airport. Common machines for goods, i.e., X-ray machines, achieve perspective imaging to obtain sharp DR images, which have formed fixed impression in the users' minds. Users have been familiar with the DR images. In a DR system, the X-ray source and detectors are fixed and irrotational. These DR images are generally images in the top angle of view or images in the bottom angle of view, which are very intuition and convenience for view. Rich experience formed from image reading and image recognition is based on these intuitional DR images. An excellent image recognizer needs to view more than several tens of thousands of actual DR images. A person generally needs to work more than 90 workdays to become an excellent image recognizer. Currently, there are numerous excellent image recognizers working in industries such as healthcare, security inspection or the like. When there is no DR image, these experienced image recognizers cannot correctly implement image recognition.

Although some existing CT systems have ready-made three-dimensional data, there is no DR image. The image recognizer may feel unaccustomed when he/she suddenly views the three-dimensional image. For example, due to an unsuitable angle of view, prohibited goods (for example, guns) may be a small agglomeration in the three-dimensional image and the pattern thereof is unclear. When the image recognizer suddenly views the three-dimensional image, he/she does not know why the guns suddenly become a small agglomeration. When the image recognizer views the three-dimensional image individually, he/she still does not know what is carried by a passenger. Therefore, even if there is a three-dimensional image, the image recognizer still wants to compare the three-dimensional image with the familiar DR image and use the existing rich experience in image recognition of the DR image. That is, the image recognizer wants to obtain such an arrangement that a display is placed on the left to display a DR image and a display is placed on the right to display a CT image. With the existing experience in image recognition of a DR image, numerous image recognizers can more rapidly, more conveniently, and more accurately know what is carried by a passenger. Thus, lots of manpower and time can be saved.

In addition, with respect to a CT device having a DR system, if a user selects a particular position, it needs to implement DR-CT registration to display a slice in the particular position. It can be known whether the particular position is on a head portion, a middle portion, or a tail portion of a luggage based on belt encoding of a hardware apparatus. However, as the belt encoding is missing or absent or cannot achieve matching in the transportation process, the method cannot accurately implement registration. There is a need for a novel and effective registration method.

SUMMARY

In view of one or more problems in the related art, an image display method in a CT system is provided, which can enable a three-dimensional image of an inspected object to be displayed together with a DR image in a case that a CT system does not have a DR imaging device.

In an aspect of the present disclosure, an image display method in a Computed Tomography (CT) system is provided, comprising steps of: implementing CT scanning on an inspected object, to obtain CT projection data; organizing the CT projection data according to a predetermined interval; extracting basic data from the organized CT projection data by using a fixed angle as a start angle and using 360 degrees as an interval; forming a Digital Radiography (DR) image based on the extracted basic data; reconstructing a three-dimensional image of the inspected object from the CT projection data; and displaying the DR image and the reconstructed three-dimensional image on a screen at the same time.

According to some embodiments, the image display method further comprises steps of: extracting complementary data from the organized CT projection data by using the fixed angle plus 180 degrees as the start angle and using 360 degrees as the interval; storing the extracted complementary data in a matrix; implementing a left-right mirror image process on the matrix; alternatively inserting the complementary data in the processed matrix into the basic data in units of rows, to obtain complemented basic data; and forming the DR image based on the complemented basic data.

According to some embodiments, the image display method further comprises steps of: extracting basic data from the organized CT projection data by using another fixed angle as a start angle and using 360 degrees as an interval; forming another DR image based on the extracted basic data; and displaying the DR image, the another DR image, and the reconstructed three-dimensional image on the screen at the same time.

According to some embodiments, the step of organizing the CT projection data according to a predetermined interval comprises: when a sampling frequency is higher than one data projection per predetermined interval, adjusting the sampling frequency of the CT projection data as one data projection per predetermined interval according to a subsampling rule; and when the sampling frequency is lower than one data projection per predetermined interval, adjusting the sampling frequency of the CT projection data as one projection data per predetermined interval according to linear interpolation.

According to some embodiments, when the basic data is high-energy data and low-energy data, the basic data is processed according to a material recognition algorithm to obtain gray-level data and material data.

According to some embodiments, the DR image is interpolated to achieve a resolution required by a user and the interpolated DR image is displayed on the screen.

According to some embodiments, data of the reconstructed three-dimensional image is one of physical density data, electron density data, atomic number data, high-energy data, low-energy data, gray-level data, and material data.

In another aspect of the present disclosure, an image display method in a Computed Tomography (CT) system is provided, comprising steps of: implementing CT scanning on an inspected object to obtain CT projection data; reconstructing a three-dimensional image of the inspected object from the CT projection data; projecting data of the three-dimensional image H(x,y,z) of the inspected object in a certain angle of view, to obtain Digital Radiography (DR) data in the angle of view, wherein the data of the three-dimensional data H(x,y,z) has a dimensional size of X×Y×Z, a dimension X changes from 1 to X in a direction perpendicular to movement of a belt in a horizontal plane, a dimension Y changes from 1 to Y in a straight-up direction, and a dimension z changes from 1 to Z in a direction along the movement of the belt in the horizontal plane; forming a DR image based on the DR data in the angle of view; and displaying the DR image and the three-dimensional image on a screen at the same time.

According to some embodiments, the image display method further comprises steps of: projecting data of the three-dimensional image H(x,y,z) of the inspected object in another angle of view, to obtain DR data in the angle of view; forming a DR image based on the DR data in the another angle of view; and displaying two DR images and the three-dimensional image on the screen at the same time.

According to some embodiments, the angle of view and the another angle of view are selected from a direction perpendicular to the movement of the belt in a horizontal plane, the straight-up direction, and the direction along the movement of the belt in the horizontal plane.

According to some embodiments, the three-dimensional data H(x,y,z) is projected along the direction of the dimension x according to the following projection equation, to obtain two-dimensional data I(y,z):

$$I(y, z) = \sum_{x=1}^{X} H(x, y, z)$$

the two-dimensional data is DR data in a side angle of view, and the data dimensional size is Y×Z.

According to some embodiments, the three-dimensional data H(x,y,z) is projected along the direction of the dimension y according to the following projection equation, to obtain two-dimensional data J(x,z):

$$J(x, y) = \sum_{y=1}^{Y} H(x, y, z)$$

the two-dimensional data is DR data in a bottom or top angle of view, and the data dimensional size is X×Z.

According to some embodiments, the three-dimensional data H(x,y,z) is projected along the direction of the dimension z, i.e., the movement of the belt, according to the following projection equation, to obtain two-dimensional data K(x,y):

$$K(x, y) = \sum_{z=1}^{Z} H(x, y, z)$$

the two-dimensional data is DR data in a front angle of view, and the data dimensional size is X×Y.

According to some embodiments, data of the reconstructed three-dimensional image is one of physical density data, electron density data, atomic number data, high-energy data, low-energy data, gray-level data, and material data.

In the above solutions, the CT projection data is processed to obtain DR data. After the DR data is obtained, a DR image is obtained directly using a DR data processing algorithm. This enables an image recognizer to more accurately and more rapidly inspect goods carried by a passenger using the existing experience in image recognition of the DR image.

In another aspect of the present disclosure, an image registration method in a Digital Radiography (DR)-Computed Tomography (CT) imaging system is provided, the DR-CT imaging system comprises a DR device and a CT device, the method comprising steps of: scanning, by the CT device, an inspected object to obtain CT projection data; reconstructing a three-dimensional image of the inspected object from the CT projection data; scanning, by the DR device, the inspected object to obtain a DR image; displaying the DR image and the three-dimensional image on a screen; extracting a corresponding column from data of the DR image in response to a user's selection of a particular position in the DR image; obtaining assistant DR data in the same angle of view as that of the DR image from the three-dimensional image; calculating correlations between the column in the DR image and various columns in the assistant DR data; and displaying a slice image corresponding to a column in the assistant DR data which has the largest correlation with the column in the DR image, on the screen together with the DR image at the same time.

According to some embodiments, the step of obtaining assistant DR data in the same angle of view as that of the DR image from the three-dimensional image comprises: projecting data of the three-dimensional image H(x,y,z) of the inspected object along the direction of the dimension y, to obtain DR data in the angle of view, wherein the data of the three-dimensional data H(x,y,z) has a dimensional size of X×Y×Z, a dimension X changes from 1 to X in a direction perpendicular to movement of a belt in a horizontal plane, a dimension Y changes from 1 to Y in a straight-up direction, and a dimension z changes from 1 to Z in a direction along the movement of the belt in the horizontal plane.

According to some embodiments, the three-dimensional data H(x,y,z) is projected along the direction of the dimension y according to the following projection equation, to obtain two-dimensional data J(x,z):

$$J(x, y) = \sum_{y=1}^{Y} H(x, y, z)$$

the two-dimensional data is DR data in a bottom or top angle of view, and the data dimensional size is X×Z.

In another aspect of the present disclosure, an image registration method in a Digital Radiography (DR)-Computed Tomography (CT) imaging system is provided, the DR-CT imaging system comprising a DR device and a CT device, the method comprising steps of: scanning, by the CT device, an inspected object to obtain CT projection data; scanning, by the DR device, the inspected object to obtain a DR image; displaying the DR image on a screen; extracting a corresponding column from data of the DR image in response to a user's selection of a particular position in the DR image; obtaining assistant DR data in the same angle of view as that of the DR image from the CT projection data;

calculating correlations between the column in the DR image and various columns in the assistant DR data; reconstructing a three-dimensional image of the inspected object from the CT projection data; and displaying a slice image corresponding to a column in the assistant DR data which has the largest correlation with the column in the DR image, on the screen together with the DR image at the same time.

According to some embodiments, the step of obtaining assistant DR data in the same angle of view as that of the DR image from the CT projection data comprises: organizing the CT projection data according to a predetermined interval; and extracting the assistant data from the organized CT projection data by using a fixed angle as a start angle and using 360 degrees as an interval.

According to some embodiments, the method further comprises steps of: extracting complementary data from the organized CT projection data by using the fixed angle plus 180 degrees as the start angle and using 360 degrees as the interval; storing the extracted complementary data in a matrix; implementing a left-right mirror image process on the matrix; and alternatively interpolating the complementary data in the processed matrix into the assistant DR data in units of rows, to obtain complemented assistant DR data.

BRIEF DESCRIPTION OF THE DRAWINGS

For better understanding the present disclosure, the present disclosure will be described in detail according to the accompanying drawings below.

DETAILED DESCRIPTION

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known circuits, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the term "and/or" used herein means any and all combinations of one or more listed items.

For problems in the related art that some CT devices do not have a DR imaging module but an image recognizer needs to display a DR image in the process of image recognition, some embodiments of the present disclosure propose obtaining a DR image of an inspected object from CT projection data and displaying the DR image on a screen together with a reconstructed three-dimensional image, for convenience of security inspection by the image recognizer using the existing experience in image recognition. According to the above solution, the goods which are carried by a passenger can be more accurately and more rapidly inspected. In some embodiments, projection data in a particular angle of view is extracted from data of the reconstructed three-dimensional image, and the projection data is combined into DR data in the angle of view. In other embodiments, the data of the reconstructed three-dimensional image is projected according to different angles of view, to obtain DR data in these angles of view, so as to form DR images.

In other embodiments, for problems that some CT devices having a DR device can not register a DR image and a CT image as belt encoding is absent or missing, it is proposed to obtain a DR image in a particular angle of view from CT projection data or data of the reconstructed three-dimensional image, and analyze correlations between a column selected from a DR image obtained by a DR device and a DR image obtained from the data of the three-dimensional image, to determine a slice where a column with the largest correlation is located and display the slice together with the DR image.

Figure 1:
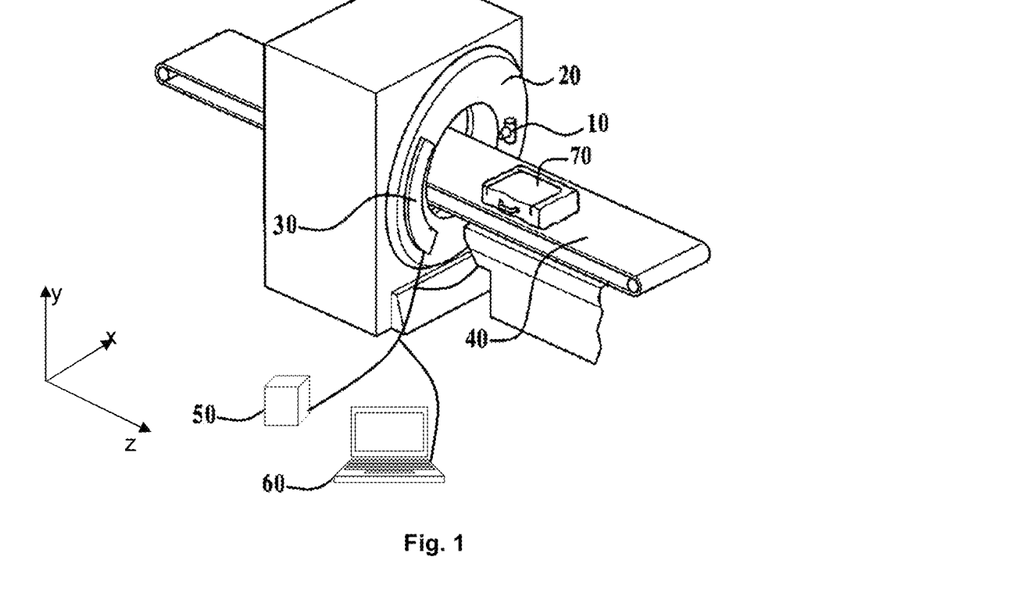
FIG. 1 illustrates a structural diagram of a CT device according to an embodiment of the present disclosure.

FIG. 1 is a structural diagram of a CT device according to an embodiment of the present disclosure. As shown in FIG. 1, the CT device according to the present embodiment comprises a rack 20, a bearing member 40, a controller 50, a computer data processor 60 or the like. The rack 20 comprises a ray source 10 to emit an X ray for inspection, for example, an X ray machine, and a detection and collection apparatus 30. The bearing member 40 bears the inspected luggage 70 to pass through a scanned area between the ray source 10 and the detection and collection apparatus 30 of the rack 20, while the rack 20 rotates around the forward direction of the inspected luggage 70. In this way, the ray emitted from the ray source 10 can transmit through the inspected luggage 70 to implement CT scanning on the inspected luggage 70.

The detection and collection apparatus 30 is for example detectors and data collectors in an integrated modular structure, such as flat panel detectors, to detect rays transmitting through the inspected liquid goods to obtain an analog signal, and convert the analog signal into a digital signal, so as to output projection data of the inspected luggage 70 with respect to the X ray. The controller 50 is configured to control various parts of the whole system to operate synchronously. The computer data processor 60 is configured to process the data collected by the data collector, process and reconstruct the data, and output a result.

As shown in FIG. 1, the ray source 10 may be placed on one side of an inspected object, and the detection and collection apparatus 30 is placed on the other side of the inspected luggage 70, including detectors and data collectors, to obtain multi-angle projection data of the inspected luggage 70. The data collector comprises a data amplification and shaping circuit, which may operate in a (current) integration manner or a pulse (counting) manner. A data output cable of the detection and collection apparatus 30 is connected to the controller 50 and the computer data processor 60, to store the collected data in the computer data processor 60 according to a trigger command.

Figure 2:
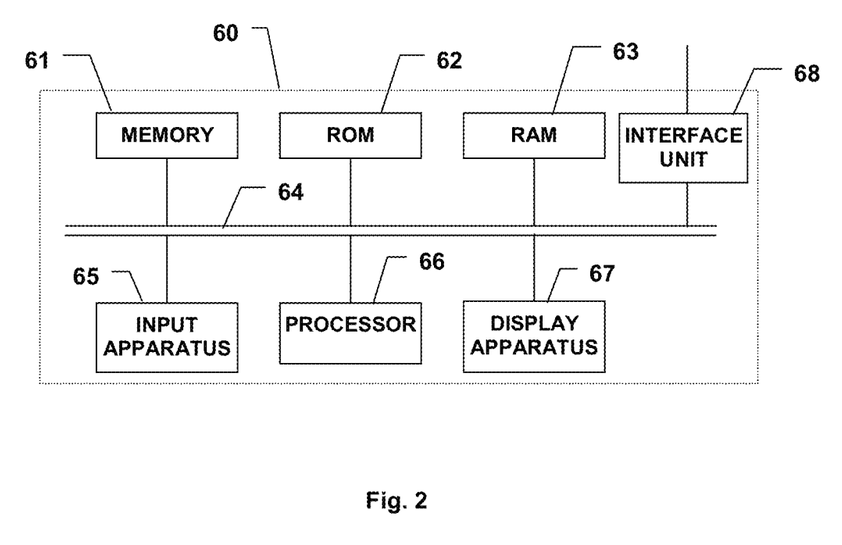
FIG. 2 illustrates a structural block diagram of a computer data processor illustrated in FIG. 1.

FIG. 2 illustrates a structural block diagram of a computer data processor 60 illustrated in FIG. 1. As shown in FIG. 2, the data collected by the data collector is stored in a memory 61 through an interface unit 68 and a bus 64. A Read-Only Memory (ROM) 62 has configuration information and programs of the computer data processor stored therein. A Random-Access Memory (RAM) 63 is configured to temporarily store various data in the operation process of a processor 66. In addition, the memory 61 also has computer programs for processing data stored therein. An internal bus 64 is configured to connect the memory 61, the ROM 62, the RAM 63, the input apparatus 65, the processor 66, the display apparatus 67, and the interface unit 68 as described above.

After a user inputs an operation command through an input apparatus 65 such as a keyboard, a mouse or the like, instruction codes of the computer program command the processor 66 to execute a predetermined data processing algorithm, and after obtaining a data processing result, display the result on a display apparatus 67 such as a Liquid Crystal Display (LCD) display or the like, or directly output the processing result in a form of hard copy such as printing.

Figure 3:
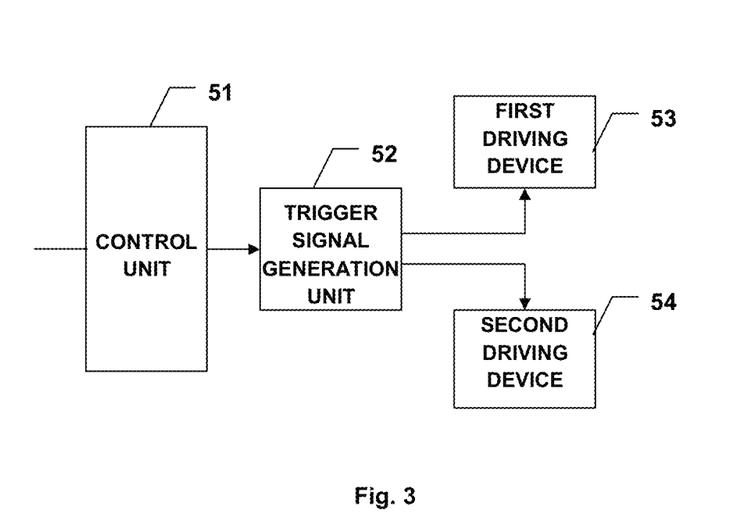
FIG. 3 illustrates a structural block diagram of a controller according to an embodiment of the present disclosure.

FIG. 3 illustrates a structural block diagram of a controller according to an embodiment of the present disclosure. As shown in FIG. 3, the controller 50 comprises a controller unit 51 configured to control the ray source 10, the bearing member 40 and the detection and collection apparatus 30 according to an instruction from the computer 60; a trigger signal generation unit 52 configured to generate a trigger command for triggering actions of the ray source 10, the detection and collection apparatus 30 and the bearing member 40 under the control of the control unit; a first driving device 53 configured to drive the bearing member 40 to transfer the inspected luggage 70 according to the trigger command generated by the trigger signal generation unit 52 under the control of the control unit 51; and a second driving device 54 configured to drive the rack 20 to rotate according to the trigger command generated by the trigger signal generation unit 52 under the control of the control unit 51. The projection data obtained by the detection and collection apparatus 30 is stored in the computer 60 for reconstruction of CT tomographic images, so as to obtain data of the tomographic images of the inspected luggage 70. Then the computer 60 obtains a DR image of the inspected luggage 70 in at least an angle of view from the data of the tomographic images by executing software, and displays the DR image together with the reconstructed three-dimensional image, for convenience of security inspection by an image recognizer. According to other embodiments, the above CT imaging system may also be a dual-energy CT system, that is, the X ray source 10 of the rack 20 may emit two rays, i.e., a high-energy ray and a low-energy ray, and after the detection and collection apparatus 30 detects projection data at different energy levels, the computer data processor 60 implements dual-energy CT reconstruction, to obtain equivalent atomic numbers and equivalent electron density data of various tomographic images of the inspected luggage 70.

Figure 4:
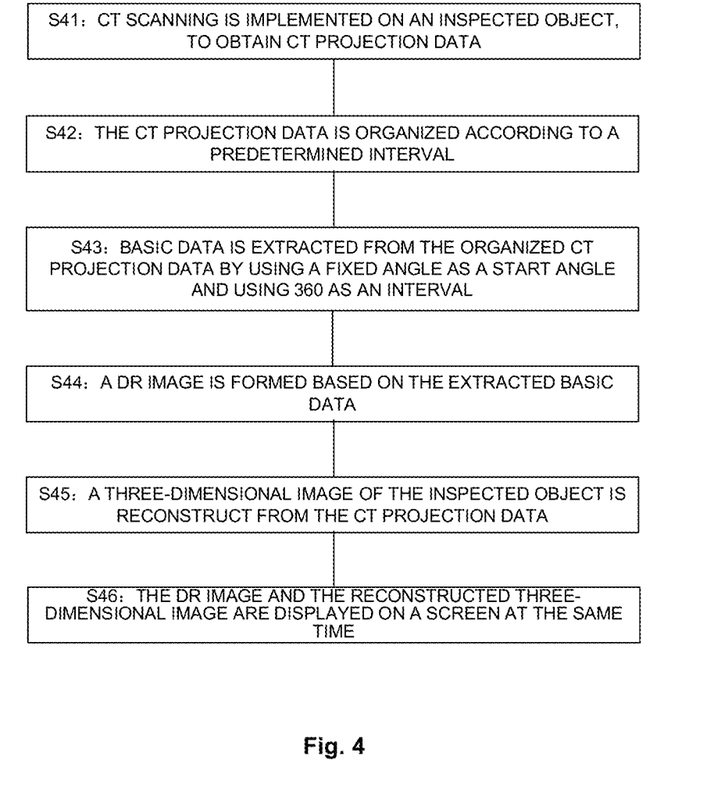
FIG. 4 is a flowchart illustrating an image display method in a CT system according to an embodiment of the present disclosure.

FIG. 4 illustrates a flowchart of an image display method in a CT system according to an embodiment of the present disclosure. As shown in FIG. 4, in step S41, a CT system implements CT scanning on an inspected object 70, to obtain CT projection data. The CT projection data here may be but is not limited to the following several data: physical density or electron density data; atomic number data; high-energy data; low-energy data; gray-level data; and material data. In the embodiment, one row of detectors is taken as an example. When there are multiple rows of detectors, the multiple rows are considered as a whole, i.e., as one row, for data processing.

In step S42, the CT projection data is organized according to a predetermined interval. For example, the CT projection data is organized using 1 degree as an interval. That is, there is one data projection per degree. In some embodiments, when a sampling frequency is higher than one data projection per degree, the sampling frequency is adjusted as one data projection per degree in accordance with a sub-sampling rule. When the sampling frequency is too low, the sampling frequency is adjusted as one data projection per degree in accordance with linear interpolation.

Figure 5:
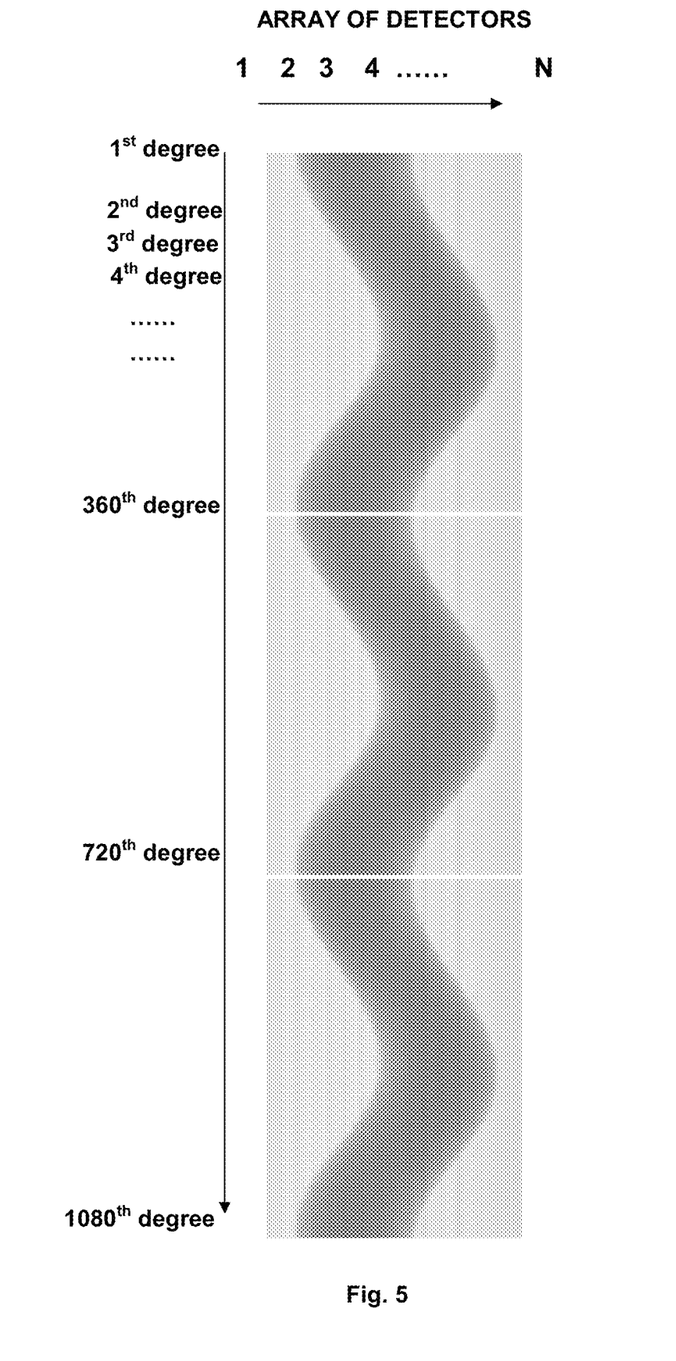
FIG. 5 is a diagram illustrating a process of organizing CT projection data.

For example, the CT projection data, i.e., the sinogram, may be organized and arranged as a matrix A, and an element in the matrix A is denoted as A(m,n). n represents an element of an array of detectors, and changes from 1-N, wherein N is a number of elements in the array of detectors m represents an angle, and a change in m represents a change in angle. That is, a first row of the matrix A is $1^{st}$-$N^{th}$ data in a first degree of the array of detectors, and a second row of the matrix A is $1^{st}$-$N^{th}$ data in a second degree of the array of detectors. All angles have a period of 360 degrees, and are periodically arranged as follows: 1-360 degrees, 361-720 degrees, 721-1080 degrees, 1081-1440 degrees, . . . , as shown in FIG. 5.

In step S43, basic data is extracted from the organized CT projection data by using a fixed angle as a start angle and using 360 as an interval. For example, data in a number of angles, for example, 1 degree, 361 degrees, 721 degrees, 1081 degrees, and 1441 degrees, is extracted from the CT projection data by using a circular period of 360 degrees as an interval and using S as a fixed start angle. That is, assume that the fixed start angle is S, in the $i^{th}$ extraction, a corresponding angle Angle is:

$$\text{Angle}=S+i\times 360 \text{ wherein } i=0,1,2,\ldots \quad (1)$$

The extracted basic data is reorganized as a matrix B.

Figure 6:
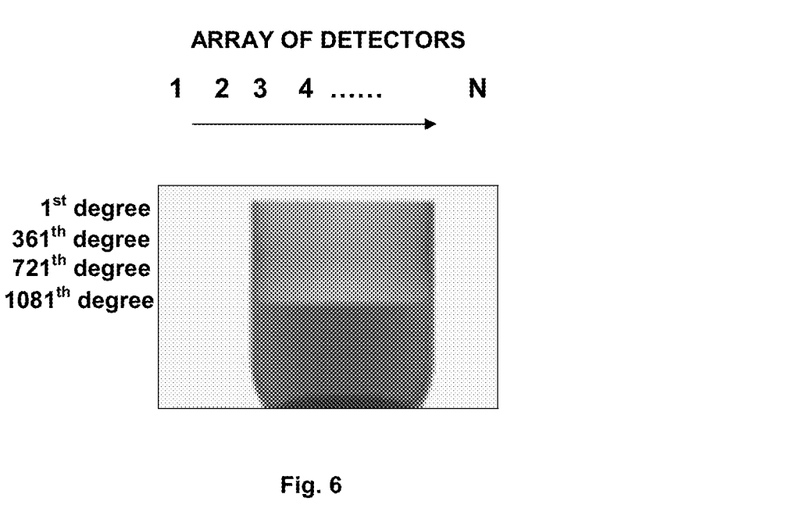
FIG. 6 illustrates a diagram of a DR image obtained from CT projection data.

In step S44, a DR image is formed based on the extracted basic data, as shown in FIG. 6. For example, the matrix B which is formed through reorganization is processed in accordance with an existing DR data processing algorithm, to form a DR image. When the data is high-energy data and low-energy data, gray-level data and material data are obtained in accordance with a material recognition algorithm.

In step S45, a computer data processor 60 executes software to reconstruct a three-dimensional image of the inspected object from the CT projection data.

In step S46, the DR image and the reconstructed three-dimensional image are displayed on a screen at the same time. In some cases, the DR image is interpolated to achieve a resolution required by a user, and the interpolated DR image is displayed on a display.

In other embodiments, if there is not enough data in the matrix B, and it needs to add data, extraction continues to be implemented in accordance with the following equation. Assume that the fixed start angle is S, in the $i^{th}$ extraction, a corresponding angle Angle is:

$$\text{Angle}=S+i\times 360+180 \text{ wherein } i=0,1,2,\ldots \qquad (2)$$

The extracted data is reorganized as a matrix B1.

Then, a left-right mirror image process is implemented on the matrix B1, i.e., symmetric elements on the left and on the right are exchanged with each other in accordance with the following equation:

$$B1(m,1)\mathord{<}\mathord{=}\mathord{=}\mathord{>}B1(m,N) \ B1(m,2)\mathord{<}\mathord{=}\mathord{=}\mathord{>}B1(m,N-1) \qquad (3)$$

Then, the obtained matrix B1 is alternatively interpolated into the matrix B in units of rows to combine with the matrix B to form a matrix C. The data dimensional size is M×N. The combination equation is as follows.

$$C(m,n) = \begin{cases} B((m+1)/2, n), & \text{when } m \text{ is an odd} \\ & \text{number 1, 3, 5, 7, \ldots} \\ B1(m/2, n), & \text{when } m \text{ is an even} \\ & \text{number 2, 4, 6, 8, \ldots} \end{cases} \qquad (4)$$

Finally, the matrix C is processed in accordance with an existing DR data processing algorithm, to form a DR image. When the data is high-energy data and low-energy data, gray-level data and material data are obtained in accordance with a material recognition algorithm.

In the above embodiment, the fixed start angle of S decides a direction of an angle of view of the DR image. For example, when S=1, a top angle of view may be obtained; when S=180, a bottom angle of view may be obtained; when S=90, a left angle of view may be obtained; and when S=270, a right angle of view may be obtained.

In the above embodiment, a DR image in one angle of view is obtained. It necessary, another fixed angle different from the above angle S may be used as a start angle to form DR data in the angle. After a corresponding DR image is obtained, the DR image is displayed on the screen together with the above DR image and the reconstructed three-dimensional image, for security inspection by an image recognizer.

In addition, in some embodiments, there may be one or more rows of detectors in a CT system, and an image in any angle of view (including a top angle of view, a bottom angle of view, and a side angle of view) may be obtained using the CT data. Alternatively, images in any two angles of view, i.e., a dual-angle of view, may be obtained using the CT data. In addition, images in any multiple angles of view, i.e., a multi-angle of view, may be obtained using the CT data.

Figure 7:
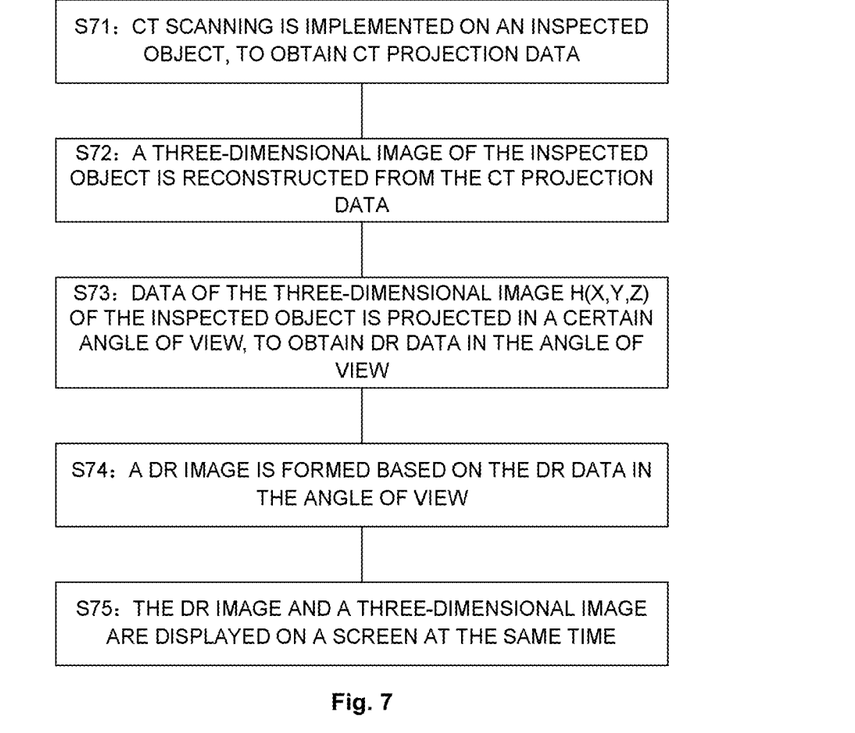
FIG. 7 is a flowchart illustrating an image display method in a CT system according to another embodiment of the present disclosure.

FIG. 7 illustrates a flowchart of an image display method in a CT system according to another embodiment of the present disclosure. As shown in FIG. 7, in step S71, a CT system implements CT scanning on an inspected object, to obtain CT projection data. Then, in step S72, a computer 60 reconstructs a three-dimensional image of the inspected object from the CT projection data. The reconstructed three-dimensional data here may be but is not limited to the following several data: physical density or electron density data; atomic number data; high-energy data; low-energy data; gray-level data; and material data.

In step S73, data of the three-dimensional image H(x,y,z) of the inspected object is projected in a certain angle of view, to obtain DR data in the angle of view, wherein the three-dimensional data H(x,y,z) has a dimensional size of X×Y×Z, a dimension X changes from 1 to X in a direction perpendicular to movement of a belt in a horizontal plane, a dimension Y changes from 1 to Y in a straight-up direction, and a dimension z changes from 1 to Z in a direction along the movement of the belt in the horizontal plane.

For example, projection is implemented in accordance with a required angle of view in the following three conditions:

(1) the three-dimensional data H(x,y,z) is projected along a direction of the dimension x according to the following projection equation, to obtain two-dimensional data I(y,z):

$$I(y,z) = \sum_{x=1}^{X} H(x,y,z) \qquad (5)$$

The two-dimensional data is DR data in the side angle of view. The data dimensional size is Y×Z.

(2) the three-dimensional data H(x,y,z) is projected along a direction of the dimension y according to the following projection equation, to obtain two-dimensional data J(x,z):

$$J(x,y) = \sum_{y=1}^{Y} H(x,y,z) \qquad (6)$$

The two-dimensional data is DR data in the bottom or top angle of view. The data dimensional size is X×Z.

(3) the three-dimensional data H(x,y,z) is projected along a direction of the dimension z, i.e., movement of a belt, according to the following projection equation, to obtain two-dimensional data K(x,y):

$$K(x,y) = \sum_{z=1}^{Z} H(x,y,z) \qquad (7)$$

The two-dimensional data is DR data in the front angle of view. The data dimensional size is X×Y.

In step S74, a DR image is formed based on the DR data in the angle of view. For example, after the DR data is obtained, the DR data is processed in accordance with an existing DR data processing algorithm to form the DR image. When the data is high-energy data and low-energy data, gray-level data and material data are obtained in accordance with a material recognition algorithm.

In step S75, the DR image and a three-dimensional image are displayed on a screen at the same time. For example, the DR image is interpolated to achieve a resolution required by a user, and the interpolated DR image is displayed on a display.

Although a condition that the CT system does not have a DR device is described above, in some CT systems having a DR device, it needs to register the DR image and a slice image. For example, a CT device having a DR system requires that after a user clicks on a certain place of the DR image, it can be determined from the three-dimensional data whether the accurate position of the slice is on a head portion, a middle portion, or a tail portion of a luggage, so as to display the slice. There are a number of slices in the three-dimensional data. In order to obtain the accurate position from the three-dimensional data to display the slice, it can be known based on the belt encoding of the hardware apparatus whether the accurate position is on a head portion, a middle portion, or a tail portion of a luggage. However, as the belt encoding is missing or absent or cannot achieve matching in the transportation process, the method cannot accurately implement registration.

For the above problems, the embodiment of the present disclosure proposes calculating a correlation between a column in the DR image obtained by the DR device and each column in the DR data extracted from the reconstructed three-dimensional image, and displaying a slice image corresponding to a column with the largest correlation on the screen together with the DR image. The DR data here may be but is not limited to the following several data: physical density or electron density data; atomic number data; high-energy data; low-energy data; gray-level data; material data etc.

Figure 8:
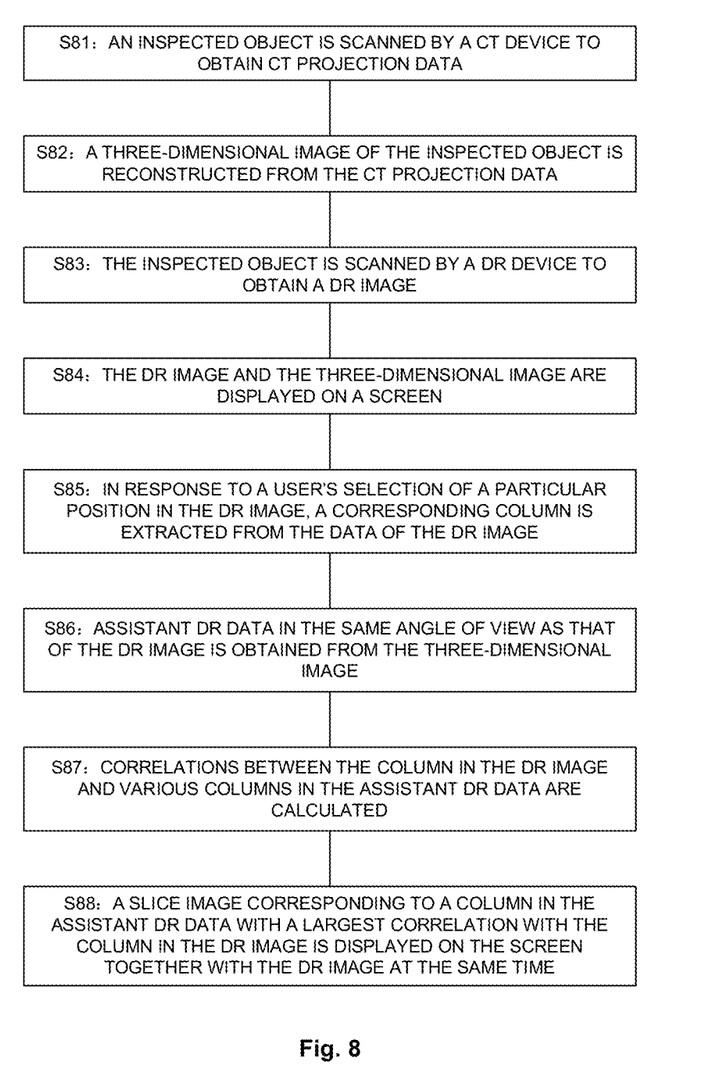
FIG. 8 is a flowchart illustrating a method for registering a DR image and a CT image in a CT system according to another embodiment of the present discourse.

FIG. 8 illustrates a flowchart of a method for registering a DR image and a CT image in a CT system according to another embodiment of the present discourse.

In step S81, an inspected object is scanned by a CT device to obtain CT projection data. In step S82, a computer 60 executes software to reconstruct a three-dimensional image of the inspected object from the CT projection data.

In step S83, the inspected object is scanned by a DR device to obtain a DR image. Then, in step S84, the obtained DR image and the reconstructed three-dimensional image are displayed on a screen, for convenience of security inspection by an image recognizer.

If the image recognizer wants to view a slice image corresponding to a certain column in the DR image, the image recognizer may operate an input apparatus 65 such as a mouse to click on the column, for convenience of more accurate inspection. In step S85, in response to a user's selection of a particular position in the DR image, a corresponding column is extracted from the data of the DR image. Next, in step S86, the computer 60 obtains assistant DR data in the same angle of view as that of the DR image from the three-dimensional image.

For example, the DR system generates DR data, and the user specifies a certain position in the DR data using a mouse. The DR data where the position is located is extended along a direction of elements of the array of detectors, and is denoted as Array0(n), wherein n changes from 1 to N. N is a number of elements in the array of detectors. The data is actually a data array, and stores data of all elements in the array of detectors.

DR data is obtained from the CT data in accordance with the method illustrated in FIG. 7, and is denoted as J, wherein the elements in J are J(x,z). The matrix J is transposed to obtain J1, wherein the elements in J1 are J1(z,x). J1 is interpolated in accordance with the required dimensional size M×N, to obtain a matrix C, which has a data dimensional size of M×N.

In some embodiments, the step of obtaining assistant DR data in the same angle of view as that of the DR image from the three-dimensional image comprises: projecting data of the three-dimensional image H(x,y,z) of the inspected object along a direction of the dimension y, to obtain DR data in the angle of view, wherein the data of the three-dimensional data H(x,y,z) has a dimensional size of X×Y×Z, a dimension X changes from 1 to X in a direction perpendicular to movement of a belt in a horizontal plane, a dimension Y changes from 1 to Y in a straight-up direction, and a dimension z changes from 1 to Z in a direction along the movement of the belt in the horizontal plane For example, the three-dimensional data H(x,y,z) is projected along the direction of the dimension y, to obtain two-dimensional data J(x,z) with reference to the above equation (6).

Then, in step S87, a computer 60 calculates correlations between the column in the DR image and various columns in the assistant DR data, and in Step S88, a slice image corresponding to a column in the assistant DR data with the largest correlation with the column in the DR image is displayed on the screen together with the DR image at the same time.

For example, a certain row is extracted from the matrix C, for example, when m=1 and n changes from 1 to N, the row is denoted as a data array Array1(n). An error E is calculated in accordance with the following equation:

$$E = \sum_{n=1}^{N} ((\text{Array1}(n) - \text{Array0}(n))^2 \qquad (8)$$

The above step is repeated. The next row is extracted, for example, when m=2 and n changes from 1 to N, the row is denoted as a data array Array1(n), until all rows in the matrix C are traversed. Finally, all E are searched one by one for m corresponding to the minimum value, and this position matches. Slice data H(x,y,z=m) is extracted from the three-dimensional data H(x,y,z) and is displayed on the display together with the DR image.

Figure 9:
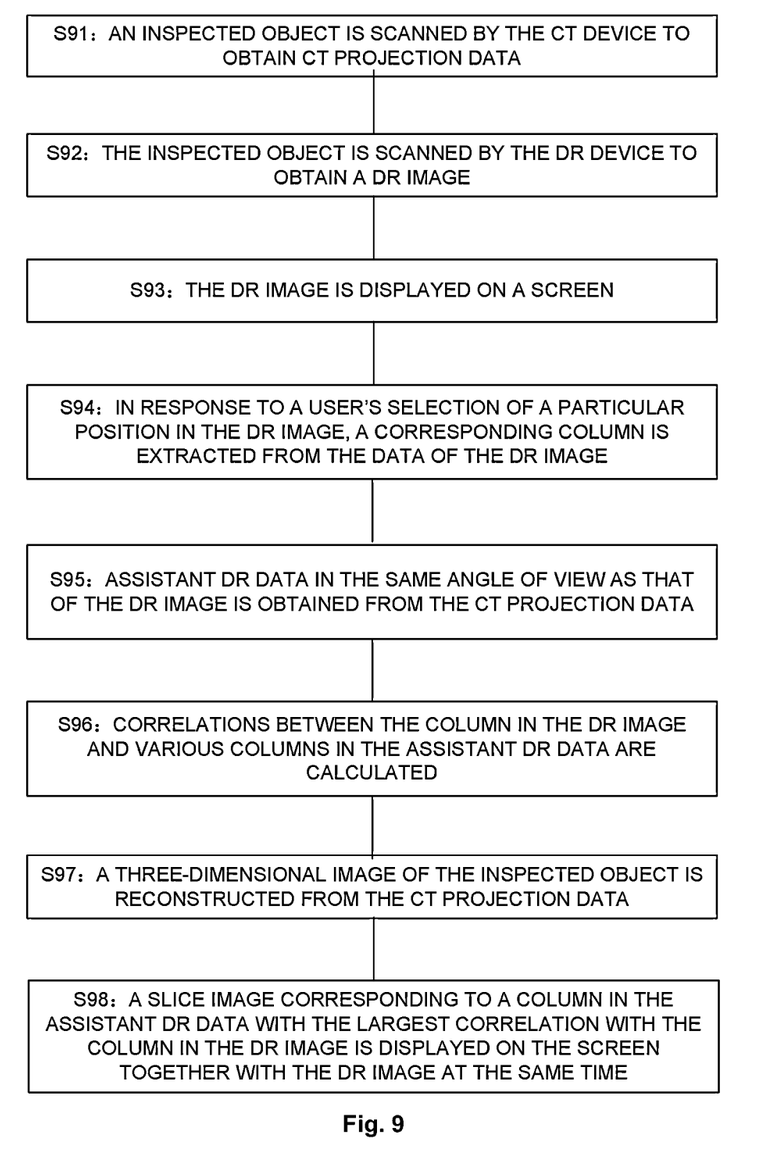
FIG. 9 is a flowchart illustrating a method for registering a DR image and a CT image in a CT system according to a further embodiment of the present discourse.

The above description relates to an embodiment of obtaining and registering assistant DR data after reconstructing the three-dimensional image. Similarly, the assistant DR data may also be obtained before the three-dimensional image is reconstructed, and then is used for image registration. FIG. 9 illustrates a flowchart of a method for registering a DR image and a CT image in a CT system according to a further embodiment of the present discourse.

In the method for image registration in the DR-CT system illustrated in FIG. 9, the DR-CT imaging system comprises a DR device and a CT device. In step S91, an inspected object is scanned by the CT device to obtain CT projection data. In step S92, the inspected object is scanned by the DR device to obtain a DR image. Then, in step S93, the DR image is displayed on a screen.

If an image recognizer wants to view a slice image corresponding to a certain column in the DR image, the image recognizer may operate an input apparatus 65 such as a mouse to click on the column, for convenience of more accurate inspection. In step S94, in response to a user's selection of a particular position in the DR image, a corresponding column is extracted from the data of the DR image.

In step S95, assistant DR data in the same angle of view as that of the DR image is obtained from the CT projection data;

in step S96, correlations between the column in the DR image and various columns in the assistant DR data are calculated;

in step S97, a three-dimensional image of the inspected object is reconstructed from the CT projection data; and in step S98, a slice image corresponding to a column in the assistant DR data with the largest correlation with the column in the DR image is displayed on the screen together with the DR image at the same time.

In some embodiments, the step of obtaining assistant DR data in the same angle of view as that of the DR image from the CT projection data comprises: organizing the CT projection data in accordance with a predetermined interval; and extracting the assistant data from the organized CT projection data by using a fixed angle as a start angle and using 360 degrees as an interval.

In other embodiments, the above method further comprises steps of extracting complementary data from the organized CT projection data by using the fixed angle plus 180 degrees as the start angle and using 360 degrees as the interval; storing the extracted complementary data in a matrix; implementing a left-right mirror image process on the matrix; and alternatively inserting the complementary data in the processed matrix into the assistant DR data in units of rows, to obtain complemented assistant DR data.

The foregoing detailed description has set forth various embodiments of the image display method and image registration method via the use of diagrams, flowcharts, and/or examples. In a case that such diagrams, flowcharts, and/or examples contain one or more functions and/or operations, it will be understood by those skilled in the art that each function and/or operation within such diagrams, flowcharts or examples may be implemented, individually and/or collectively, by a wide range of structures, hardware, software, firmware, or virtually any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

We claim:

1. An image display method in a Computed Tomography (CT) system, comprising steps of:
   implementing CT scanning on an inspected object, to obtain CT projection data;
   organizing the CT projection data according to a predetermined interval;
   extracting basic data from the organized CT projection data by using a fixed angle as a start angle and using 360 degrees as an interval;
   forming a Digital Radiography (DR) image based on the extracted basic data;
   reconstructing a three-dimensional image of the inspected object from the CT projection data; and
   displaying the DR image and the reconstructed three-dimensional image on a screen at the same time.

2. The image display method according to claim 1, further comprising steps of:
   extracting complementary data from the organized CT projection data by using the fixed angle plus 180 degrees as the start angle and using 360 degrees as the interval;
   storing the extracted complementary data in a matrix;
   implementing a left-right mirror image process on the matrix;
   alternatively inserting the complementary data in the processed matrix into the basic data in units of rows, to obtain complemented basic data; and
   forming the DR image based on the complemented basic data.

3. The image display method according to claim 1, further comprising steps of:
   extracting basic data from the organized CT projection data by using another fixed angle as a start angle and using 360 degrees as an interval;
   forming another DR image based on the extracted basic data; and
   displaying the DR image, the another DR image, and the reconstructed three-dimensional image on the screen at the same time.

4. The image display method according to claim 1, the step of organizing the CT projection data according to a predetermined interval comprises:
   when a sampling frequency is higher than one data projection per predetermined interval, adjusting the sampling frequency of the CT projection data as one data projection per predetermined interval according to a sub-sampling rule; and
   when the sampling frequency is lower than one data projection per predetermined interval, adjusting the sampling frequency of the CT projection data as one projection data per predetermined interval according to linear interpolation.

5. The image display method according to claim 1, when the basic data is high-energy data and low-energy data, the basic data is processed according to a material recognition algorithm to obtain gray-level data and material data.

6. The image display method according to claim 1, wherein the DR image is interpolated to achieve a resolution required by a user and the interpolated DR image is displayed on the screen.

7. The image display method according to claim 1, wherein data of the reconstructed three-dimensional image is one of physical density data, electron density data, atomic number data, high-energy data, low-energy data, gray-level data, and material data.

8. An image display method in a Computed Tomography (CT) system, comprising steps of:
   implementing CT scanning on an inspected object to obtain CT projection data;

reconstructing a three-dimensional image of the inspected object from the CT projection data;
projecting data of the three-dimensional image H(x,y,z) of the inspected object in a certain angle of view, to obtain Digital Radiography (DR) data in the angle of view, wherein the data of the three-dimensional data H(x,y,z) has a dimensional size of X×Y×Z, a dimension X changes from 1 to X in a direction perpendicular to movement of a belt in a horizontal plane, a dimension Y changes from 1 to Y in a straight-up direction, and a dimension z changes from 1 to Z in a direction along the movement of the belt in the horizontal plane;
forming a DR image based on the DR data in the angle of view; and
displaying the DR image and the three-dimensional image on a screen at the same time.

9. The image display method according to claim 8, further comprising steps of:
projecting data of the three-dimensional image H(x,y,z) of the inspected object in another angle of view, to obtain DR data in the angle of view;
forming a DR image based on the DR data in the another angle of view; and
displaying two DR images and the three-dimensional image on the screen at the same time.

10. The image display method according to claim 8, wherein the angle of view and the another angle of view are selected from a direction perpendicular to the movement of the belt in a horizontal plane, the straight-up direction, and the direction along the movement of the belt in the horizontal plane.

11. The image display method according to claim 8, wherein the three-dimensional data H(x,y,z) is projected along the direction of the dimension x according to the following projection equation, to obtain two-dimensional data I(y,z):

$$I(y, z) = \sum_{x=1}^{X} H(x, y, z)$$

the two-dimensional data is DR data in a side angle of view, and the data dimensional size is Y×Z.

12. The image display method according to claim 8, wherein the three-dimensional data H(x,y,z) is projected along the direction of the dimension y according to the following projection equation, to obtain two-dimensional data J(x,z):

$$J(x, y) = \sum_{y=1}^{Y} H(x, y, z)$$

the two-dimensional data is DR data in a bottom or top angle of view, and the data dimensional size is X×Z.

13. The image display method according to claim 8, wherein the three-dimensional data H(x,y,z) is projected along the direction of the dimension z, i.e., the movement of the belt, according to the following projection equation, to obtain two-dimensional data K(x,y):

$$K(x, y) = \sum_{z=1}^{Z} H(x, y, z)$$

the two-dimensional data is DR data in a front angle of view, and the data dimensional size is X×Y.

14. The image display method according to claim 8, wherein data of the reconstructed three-dimensional image is one of physical density data, electron density data, atomic number data, high-energy data, low-energy data, gray-level data, and material data.

15. An image registration method in a Digital Radiography (DR)-Computed Tomography (CT) imaging system, the DR-CT imaging system comprising a DR device and a CT device, the method comprising steps of:
scanning, by the CT device, an inspected object to obtain CT projection data;
reconstructing a three-dimensional image of the inspected object from the CT projection data;
scanning, by the DR device, the inspected object to obtain a DR image;
displaying the DR image and the three-dimensional image on a screen;
extracting a corresponding column from data of the DR image in response to a user's selection of a particular position in the DR image;
obtaining assistant DR data in the same angle of view as that of the DR image from the three-dimensional image;
calculating correlations between the column in the DR image and various columns in the assistant DR data; and
displaying a slice image corresponding to a column in the assistant DR data which has the largest correlation with the column in the DR image, on the screen together with the DR image at the same time.

16. The method according to claim 15, wherein the step of obtaining assistant DR data in the same angle of view as that of the DR image from the three-dimensional image comprises:
projecting data of the three-dimensional image H(x,y,z) of the inspected object along the direction of the dimension y, to obtain DR data in the angle of view, wherein the data of the three-dimensional data H(x,y,z) has a dimensional size of X×Y×Z, a dimension X changes from 1 to X in a direction perpendicular to movement of a belt in a horizontal plane, a dimension Y changes from 1 to Y in a straight-up direction, and a dimension z changes from 1 to Z in a direction along the movement of the belt in the horizontal plane.

17. The method according to claim 16, wherein the three-dimensional data H(x,y,z) is projected along the direction of the dimension y according to the following projection equation, to obtain two-dimensional data J(x,z):

$$J(x, y) = \sum_{y=1}^{Y} H(x, y, z)$$

the two-dimensional data is DR data in a bottom or top angle of view, and the data dimensional size is X×Z.

18. An image registration method in a Digital Radiography (DR)-Computed Tomography (CT) imaging system, the DR-CT imaging system comprising a DR device and a CT device, the method comprising steps of:
scanning, by the CT device, an inspected object to obtain CT projection data;
scanning, by the DR device, the inspected object to obtain a DR image;

displaying the DR image on a screen;

extracting a corresponding column from data of the DR image in response to a user's selection of a particular position in the DR image;

obtaining assistant DR data in the same angle of view as that of the DR image from the CT projection data;

calculating correlations between the column in the DR image and various columns in the assistant DR data;

reconstructing a three-dimensional image of the inspected object from the CT projection data; and displaying a slice image corresponding to a column in the assistant DR data which has the largest correlation with the column in the DR image, on the screen together with the DR image at the same time.

19. The method according to claim 18, wherein the step of obtaining assistant DR data in the same angle of view as that of the DR image from the CT projection data comprises:

organizing the CT projection data according to a predetermined interval; and extracting the assistant data from the organized CT projection data by using a fixed angle as a start angle and using 360 degrees as an interval.

20. The method according to claim 19, further comprising steps of:

extracting complementary data from the organized CT projection data by using the fixed angle plus 180 degrees as the start angle and using 360 degrees as the interval;

storing the extracted complementary data in a matrix;

implementing a left-right mirror image process on the matrix; and alternatively interpolating the complementary data in the processed matrix into the assistant DR data in units of rows, to obtain complemented assistant DR data.

* * * * *